(12) United States Patent
Lalezari et al.

(10) Patent No.: US 8,034,966 B1
(45) Date of Patent: Oct. 11, 2011

(54) PHENOXYISOBUTYRIC ACID COMPOUNDS AND METHODS FOR SYNTHESIS

(75) Inventors: Iraj Lalezari, Louisville, CO (US); Jill Fabricant, Corona del Mar, CA (US)

(73) Assignee: Cell Viable Corporation, Corona del Mar, CA (US)

( * ) Notice: Subject to any disclaimer, the term of this patent is extended or adjusted under 35 U.S.C. 154(b) by 322 days.

(21) Appl. No.: 12/380,020

(22) Filed: May 15, 2009

Related U.S. Application Data

(60) Provisional application No. 61/066,330, filed on Feb. 20, 2008.

(51) Int. Cl.
*C07C 69/96* (2006.01)
*C07C 229/00* (2006.01)

(52) U.S. Cl. ........................................ 558/260; 562/455
(58) Field of Classification Search .................. 558/260; 562/455
See application file for complete search history.

(56) References Cited

U.S. PATENT DOCUMENTS

2007/0099966 A1* 5/2007 Fabricant ....................... 514/350
2008/0076804 A1* 3/2008 Fabricant ....................... 514/348
* cited by examiner

*Primary Examiner* — Jafar Parsa
(74) *Attorney, Agent, or Firm* — Hedman & Costigan, P.C.; James V. Costigan

(57) ABSTRACT

The present invention provides a process for the synthesis of substituted arylureidophenoxymethylpropionic acid and related compounds including bifunctional and tetrafunctional derivatives. The compounds are useful for inhibiting the formation of AGEs (Aminaglycation end products).

8 Claims, 4 Drawing Sheets

PHENOXYISOBUTYRIC ACID COMPOUNDS AND METHODS FOR SYNTHESIS

This application claims priority to provisional application Ser. No. 61/066,330, filed Feb. 20, 2008.

BACKGROUND OF THE INVENTION

The present invention relates generally to the synthesis and production of novel substituted arylureidophenoxymethylpropionic acids that are useful in pharmaceutical applications. One use of the disclosed compounds is as anti AGE (Aminaglycation End Products) compound for the treatment of diabetes.

It is known in the art that elevated concentration of reducing sugars in the blood and in the intracellular environment results in the nonenzymatic formation of glycation and dehydration condensation complexes known as advanced glycation end-products or aminaglycation end products (AGEs). Nonenzymatic glycation is a complex series of reactions between reducing sugars and amino groups of proteins, lipids, and DNA. These complex products form on free amino groups on proteins, on lipids and on DNA (Bucala and Cerami, 1992; Bucala et al., 1993; Bucala et al., 1984). This phenomenon is called "browning" or a "Maillard" reaction and was discovered early in this century by the food industry (Maillard, 1916). The reaction is initiated with the reversible formation of Schiff's base which undergoes rearrangement to form a stable Amadori product. Both Schiff's base and Amadori product further undergo a series of reactions through dicarbonyl intermediates to form AGEs. The significance of a similar process in biology became evident only after the discovery of the glycosylated hemoglobins and their increased presence in diabetic patients (Rahbar, 1968; Rahbar et al., 1969). In human diabetic patients and in animal models of diabetes, these nonenzymatic reactions are accelerated and cause increased AGE formation and increased glycation of long-lived proteins such as collagen, fibronectin, tubulin, lens crystallin, myelin, laminin and actin, in addition to hemoglobin and albumin, and also of LDL associated lipids and apoprotein. Moreover, brown pigments with spectral and fluorescent properties similar to those of late-stage Maillard products have also been found in vivo in association with several long-lived proteins such as crystalline lens proteins and collagen from aged individuals. An age-related linear increase in pigments was observed in human dura collagen between the ages of 20 to 90 years. AGE modified proteins increase slowly with aging and are thought to contribute to normal tissue remodeling. Their level increases markedly in diabetic patients as a result of sustained high blood sugar levels and lead to tissue damage through a variety of mechanisms including alteration of tissue protein structure and function, stimulation of cellular responses through AGE specific receptors or the generation of reactive oxygen species (ROS) (for a recent review see Boel et al., 1995). The structural and functional integrity of the affected molecules, which often have major roles in cellular functions, become disturbed by these modifications, with severe consequences on affected organs such as kidney, eye, nerve, and micro-vascular functions (Silbiger et al., 1993; Brownlee et al., 1985).

Structural changes on macromolecules by AGEs are known to accumulate under normal circumstances with increasing age. This accumulation is severely accelerated by diabetes and is strongly associated with hyperglycemia. For example, formation of AGE on protein in the subendothelial basement membrane causes extensive cross-link formation which leads to severe structural and functional changes in protein/protein and protein/cell interaction in the vascular wall (Haitoglou et al., 1992; Airaksinen et al., 1993).

Enhanced formation and accumulation of advanced glycation end products (AGEs) have been implicated as a major pathogenesis process leading to diabetic complications, normal aging, atherosclerosis and Alzheimer's disease. This process is accelerated by diabetes and has been postulated to contribute to the development of a range of diabetic complications including nephropathy (Nicholls and Mandel, 1989), retinopathy (Hammes et al., 1991) and neuropathy (Cameron et al., 1992). Particularly, tissue damage to the kidney by AGEs leads to progressive decline in renal function, end-stage renal disease (ESRD) (Makita et al., 1994), and accumulation of low-molecular-weight (LMW) AGE peptides (glycotoxins) (Koschinsky et al., 1997) in the serum of patients with ESRD (Makita et al., 1991). These low molecular weight (LMW)-AGEs can readily form new crosslinks with plasma or tissue components, e.g., low density lipoprotein (LDL) (Bucala et al., 1994) or collagen (Miyata et al., 1993) and accelerate the progression of tissue damage and morbidity in diabetics.

Direct evidence indicating the contribution of AGEs in the progression of diabetic complications in different lesions of the kidneys, the rat lens and in atherosclerosis has been reported (Vlassara et al., 1994; Vlassara et al., 1995; Horie et al., 1997; Matsumoto et al., 1997; Soulis-Liparota et al., 1991; Bucala and Vlassara, 1997; Bucala and Rahbar, 1998; Park et al., 1998). Indeed, the infusion of pre-formed AGEs into healthy rats induces glomerular hypertrophy and mesangial sclerosis, gene expression of matrix proteins and production of growth factors (Brownlee et al., 1991; Vlassara et al., 1995). Several lines of evidence indicate that the increase in reactive carbonyl intermediates (methylglyoxal, glycolaldehyde, glyoxal, 3-deoxyglucosone, malondialdehyde and hydroxynonenal) is the consequence of hyperglycemia in diabetes. "Carbonyl stress" leads to increased modification of proteins and lipids, followed by oxidant stress and tissue damage (Baynes and Thorpe, 1999; Onorato et al., 1998; McLellan et al., 1994). Further studies have revealed that aminoguanidine (AG), an inhibitor of AGE formation, ameliorates tissue impairment of glomeruli and reduces albuminuria in induced diabetic rats (Soulis-Liparota et al., 1991; Itakura et al., 1991). In humans, decreased levels of hemoglobin (Hb)-AGE (Makita et al., 1992) concomitant with amelioration of kidney function as the result of aminoguanidine therapy in diabetic patients, provides more evidence for the importance of AGEs in the pathogenesis of diabetic complications (Bucala and Vlassara, 1997).

The global prevalence of diabetes mellitus, in particular in the United States, afflicting millions of individuals with significant increases of morbidity and mortality, together with the great financial burden for the treatment of diabetic complications in this country, are major incentives to search for and develop drugs with a potential for preventing or treating complications of the disease. So far the mechanisms of hyperglycemia-induced tissue damage in diabetes are not well understood. However, four pathogenic mechanisms have been proposed, including increased polyol pathway activity, activation of specific protein kinase C (PKC) isoforms, formation and accumulation of advanced glycation endproducts, and increased generation of reactive oxygen species (ROS) (Kennedy and Lyons, 1997). Most recent immunohistochemical studies on different tissues from kidneys obtained from ESRD patients (Horie et al., 1997) and diabetic rat lenses (Matsumoto et al., 1997), by using specific antibodies against carboxymethyllysine (CML), pentosidine, the two known glycoxidation products and pyrraline, have localized these AGE components in different lesions of the kidneys and the rat lens, and have provided more evidence in favor of protein-AGE formation in close association with generation of ROS to be major factors in causing permanent and irreversible modification of tissue proteins. Therefore, inhibitors of AGE formation and antioxidants hold promise as effective means of prevention and treatment of diabetic complications.

The Diabetic Control and Complications Trial (DCCT), has identified hyperglycemia as the main risk factor for the development of diabetic complications (The Diabetes Control and Complications Trial Research Group, 1993). Compelling evidence identifies the formation of advanced glycation endproducts as the major pathogenic link between hyperglycemia and the long-term complications of diabetes (Makita et al., 1994; Koschinsky et al., 1997; Makita et al., 1993; Bucala et al., 1994; Bailey et al., 1998).

The reactions between reducing sugars and amino groups of proteins, lipids and DNA undergo a series of reactions through dicarbonyl intermediates to generate advanced glycation endproducts (Bucala and Cerami, 1992; Bucala et al., 1993; Bucala et al., 1984).

In human diabetic patients and in animal models of diabetes, AGE formation and accumulation of long-lived structural proteins and lipoproteins have been reported. Most recent reports indicate that glycation inactivates metabolic enzymes (Yan and Harding, 1999; Kato et al., 2000; Verbeke et al., 2000; O'Harte et al., 2000). The glycation-induced change of immunoglobin G is of particular interest. Reports of glycation of the Fab fragment of IgG in diabetic patients suggest that immune deficiency observed in these patients may be explained by this phenomenon (Lapolla et al., 2000). Furthermore, an association between IgM response to IgG damaged by glycation and disease activity in rheumatoid arthritis has been reported (Lucey et al., 2000). Also, impairment of high-density lipoprotein function by glycation has been described (Hedrick et al., 2000).

Methylglyoxal (MG) has recently received considerable attention as a common mediator and the most reactive dicarbonyl to form AGEs (Phillips and Thornalley, 1993; Beisswenger et al., 1998). It is also a source of reactive oxygen species (ROS) (free radicals) generation in the course of glycation reactions (Yim et al., 1995).

Nature has devised several humoral and cellular defense mechanisms to protect tissues from the deleterious effects of "carbonyl stress" and accumulation of AGEs, e.g., the glyoxylase systems (I and II) and aldose reductase catalyze the detoxification of MG to D-lactate (McLellan et al., 1994). Amadoriases are also a novel class of enzymes found in *Aspergillus* which catalyze the deglycation of Amadori products (Takahashi et al., 1997). Furthermore, several AGE-receptors have been characterized on the surface membranes of monocytes and on macrophage, endothelial, mesangial and hepatic cells. One of these receptors, RAGE, a member of the immunoglobulin superfamily, has been found to have a wide tissue distribution (Schmidt et al., 1994; Yan et al., 1997). The discovery of various natural defense mechanisms against glycation and AGE formation suggests an important role of AGEs in the pathogenesis of vascular and peripheral nerve damage in diabetes. MG binds to and irreversibly modifies arginine and lysine residues in proteins. MG modified proteins have been shown to be ligands for the AGE receptor (Westwood et al., 1997) indicating that MG modified proteins are analogous (Schalkwijk et al., 1998) to those found in AGEs. Furthermore, glycolaldehyde, a reactive intermediate in AGE formation, generates an active ligand for macrophage scavenger receptor (Nagai et al., 2000). The effects of MG on LDL have been characterized in vivo and in vitro (Bucala et al., 1993).

Lipid peroxidation of polyunsaturated fatty acids (PUFA), such as arachidonate, also yields carbonyl compounds; some are identical to those formed from carbohydrates (Al-Abed et al., 1996), such as MG and GO, and others are characteristic of lipids, such as malondialdehyde (MDA) and 4-hydroxynonenal (HNE) (Requena et al., 1997). The latter two carbonyl compounds produce lipoxidation products (Al-Abed et al., 1996; Requena et al., 1997). A recent report emphasizes the importance of lipid-derived MDA in the cross-linking of modified collagen and in diabetes mellitus (Slatter et al., 2000). A number of AGE compounds, both fluorophores and nonfluorescent, are involved in crosslinking proteins and have been characterized (Baynes and Thorpe, 1999). In addition to glucose derived AGE-protein crosslinks, AGE crosslinking also occurs between tissue proteins and AGE-containing peptide fragments formed from AGE-protein digestion and turnover. These reactive AGE-peptides, now called glycotoxins, are normally cleared by the kidneys. In diabetic patients, these glycotoxins react with the serum proteins and are a source for widespread tissue damage (He et al., 1999).

However, detailed information on the chemical nature of the crosslink structures remain unknown. The crosslinking structures characterized to date, on the basis of chemical and spectroscopic analyses, constitute only a small fraction of the AGE crosslinks which occur in vivo, with the major crosslinking structure(s) still unknown. Most recently, a novel acid-labile AGE-structure, N-omega-carboxymethylarginine (CMA), has been identified by enzymatic hydrolysis of collagen. Its concentration was found to be 100 times greater than the concentration of pentosidine (Iijima et al., 2000) and it is assumed to be a major AGE crosslinking structure.

In addition to aging and diabetes, the formation of AGEs has been linked with several other pathological conditions. IgM anti-IgG-AGE appears to be associated with clinical measurements of rheumatoid arthritis activity (Lucey et al., 2000). A correlation between AGEs and rheumatoid arthritis was also made in North American Indians (Newkirk et al., 1998). AGEs are present in brain plaques in Alzheimer's disease and the presence of AGEs may help promote the development of Alzheimer's disease (Durany et al., 1999; Munch et al., 1998; Munch et al., 1997). Uremic patients have elevated levels of serum AGEs compared to age-matched controls (Odani et al., 1999; Dawnay and Millar, 1998). AGEs have also been correlated with neurotoxicity (Kikuchi et al., 1999). AGE proteins have been associated with atherosclerosis in mice (Sano et al., 1999) and with atherosclerosis in persons undergoing hemodialysis (Takayama et al., 1998). A study in which aminoguanidine was fed to rabbits showed that increasing amounts of aminoguanidine led to reduced plaque formation in the aorta thus suggesting that advanced glycation may participate in atherogenesis and raising the possibility that inhibitors of advanced glycation may retard the process (Panagiotopoulos et al., 1998). Significant deposition of N(epsilon)-carboxymethyl lysine (CML), an advanced glycation endproduct, is seen in astrocytic hyaline inclusions in persons with familial amyotrophic lateral sclerosis but is not seen in normal control samples (Kato et al., 1999; Shibata et al., 1999). Cigarette smoking has also been linked to increased accumulation of AGEs on plasma low density lipoprotein, structural proteins in the vascular wall, and the lens proteins of the eye, with some of these effects possibly leading to pathogenesis of atherosclerosis and other diseases associated with tobacco usage (Nicholl and Bucala, 1998). Finally, a study in which aminoguanidine was fed to rats showed that the treatment protected against progressive cardiovascular and renal decline (Li et al., 1996).

The mechanism of the inhibitory effects of aminoguanidine in the cascade of glycosylation events has been investigated. To date, the exact mechanism of AG-mediated inhibition of AGE formation is not completely known. Several lines of in vitro experiments resulted in contrasting conclusions. Briefly, elevated concentrations of reducing sugars cause reactions between carbohydrate carbonyl and protein amino groups leading to: 1. Reversible formation of Schiff's bases followed by 2. Amadori condensation/dehydration products such as 3-deoxyglucason (3-DG), a highly reactive dicarbonyl compound (Kato et al., 1990). 3. Irreversible and highly reactive advanced glycosylation endproducts. Examples of early Amadori products are ketoamines which undergo further condensation reactions to form late AGEs. A number of AGE products have been purified and characterized recently, each one constituting only minor fractions of the in vivo generated AGEs. Examples are pyrraline, pentosidine, carboxymethyl-lysine (CML), carboxyethyl-lysine (CEL), crossline, pyrrolopyridinium, methylglyoxal lysine dimer (MOLD), Arg-Lys imidazole, arginine pyridinium, cypentodine, piperidinedinone enol and alkyl, formyl, diglycosyl-pyrrole (Vlassara, 1994).

Analysis of glycation products formed in vitro on a synthetic peptide has demonstrated that aminoguanidine does not inhibit formation of early Amadori products (Edelstein and Brownlee, 1992). Similar conclusions were reached by analysis of glycation products formed on BSA (Requena et al., 1993). In both experiments AGE formation was strongly inhibited by AG as analyzed by fluorescence measurements and by mass spectral analysis. The mass spectral analysis did not detect peptide complexes with molecular mass corresponding to an incorporation of AG in the complex. Detailed mechanistic studies using NMR, mass spectroscopy and X-ray diffraction have shown that aminoguani dine reacts with AGE precursor 3-DG to form 3-amino-5- and 3-amino-6-substituted triazines (Hirsch et al., 1992). In contrast, other experiments using labeled .sup.14C-AG with lens proteins suggest that AG becomes bound to the proteins and also reacts with the active aldose form of free sugars (Harding, 1990).

Several other potential drug candidates as AGE inhibitors have been reported. These studies evaluated the agent's ability to inhibit AGE formation and AGE-protein crosslinking compared to that of aminoguanidine (AG) through in vitro and in vivo evaluations (Nakamura et al., 1997; Kochakian et al., 1996). A recent breakthrough in this field is the discovery of a compound, N-phenacylthiazolium bromide (PTB), which selectively cleaves AGE-derived protein crosslinks in vitro and in vivo (Vasan et al., 1996; Ulrich and Zhang, 1997). The pharmacological ability to break irreversible AGE-mediated protein crosslinking offers potential therapeutic use.

It is well documented that early pharmaceutical intervention against the long-term consequences of hyperglycemia-induced crosslinking prevent the development of severe late complications of diabetes. The development of nontoxic and highly effective drugs that completely stop glucose-mediated crosslinking in the tissues and body fluids is a highly desirable goal. The prototype of the pharmaceutical compounds investigated both in vitro and in vivo to intervene with the formation of AGEs on proteins is aminoguanidine (AG), a small hydrazine-like compound (Brownlee et al., 1986). However, a number of other compounds were found to have such an inhibitory effect on AGE formation. Examples are D-lysine. (Sensi et al., 1993), desferrioxamine (Takagi et al., 1995), D-penicillamine (McPherson et al., 1988), thiamine pyrophosphate and pyridoxamine (Booth et al., 1997) which have no structural similarities to aminoguanidme.

Clinical trials of AG as the first drug candidate intended to inhibit AGE formation are in progress (Corbett et al., 1992). A number of hydrazine-like and non-hydrazine compounds have been investigated. So far AG has been found to be the most useful with fewer side effects than other tested compounds of the prior art. AG is also a well known selective inhibitor of nitric oxide (NO) and can also have antioxidant effects (Tilton et al., 1993).

A number of other potential drug candidates to be used as AGE inhibitors have been discovered recently and evaluated both in vitro and in vivo (Nakamura et al., 1997; Soulis et al., 1997). While the success in studies with aminoguanidine and similar compounds is promising, the need to develop additional inhibitors of AGEs continues to exist in order to broaden the availability and the scope of this activity and therapeutic utility.

SUMMARY OF THE INVENTION

The compounds of the present invention have the following formula:

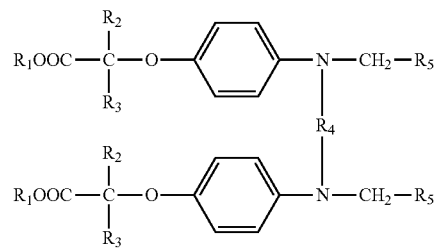

wherein $R_1$ is selected from hydrogen and a pharmaceutically acceptable cation;

$R_2$ and $R_3$ are independently selected from hydrogen and lower alkyl of 1 to 5 carbon atoms;

$R_4$ is —CO—NH($R_6$)$_n$NH—CO—, —CO—NH($R_6$)$_n$—CO—, —CO—NH($R_6$)$_n$—, —CO—($R_6$)$_n$—CO—, or —($R_6$)$_n$—, wherein $R_6$ is phenylene, or a straight, branched or cyclic alkyl with 1 to 6 carbon atoms and n is a whole integer from 1 to 4;

$R_5$ is independently selected from phenylene; mono-, di-, and tri-alkyl or haloalkyl phenylene of 1 to 5 carbon atoms; mono-, di- and tri halophenylene; phenylene-$CH_2$-phenylene or a phenoxyisobutyric acid derivative of the formula;

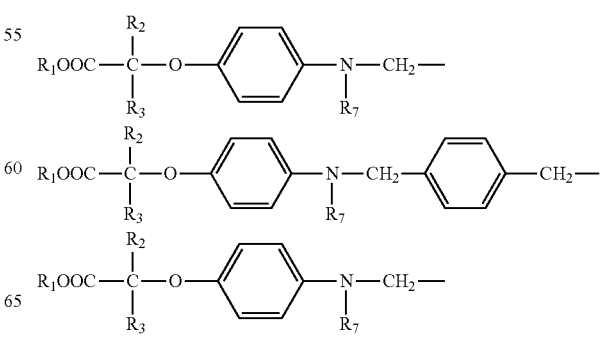

-continued

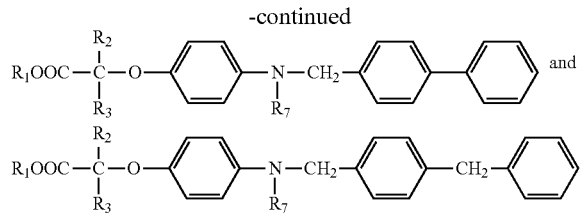

wherein $R_1$, $R_2$ and $R_3$ are as previously defined and $R_7$ is hydrogen, lower alkyl of 1-4 carbon atoms or $R_4$ when both $R_5$ moieties are the phenoxyisobutyric acid derivatives.

DETAILED DESCRIPTION OF THE INVENTION

Figure 1:
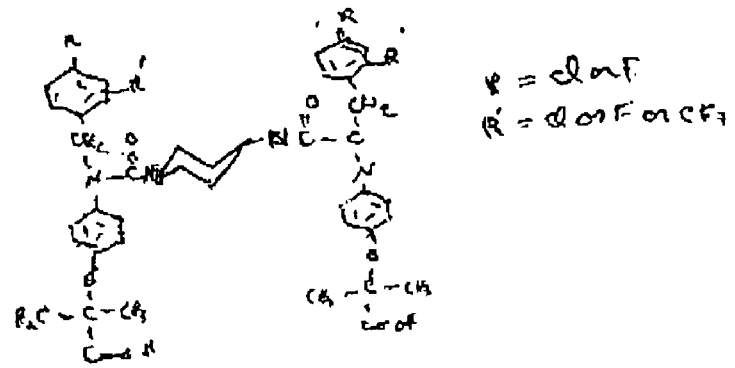
FIG. 1 shows the structure of one embodiment of the present invention.

The present inventor has previously reported new classes of compounds which are aryl (and heterocyclic) ureido and aryl (and heterocyclic) carboxamido phenoxyisobutyric acids and also benzoic acid derivatives and related compounds as inhibitors of glycation and AGE formation (Rahbar et al., 1999; Rahbar et al., 2000; Rahbar et al., 2002). See also U.S. Pat. Nos. 5,093,367; 6,072,072; 6,337,350; 6,605,642 and 7,030,133 which are incorporated herein by reference. An elevated concentration of reducing sugars (i.e., glucose) in the blood and in the intracellular environment of an animal, namely a human, typically results in the nonenzymatic formation of glycation and dehydration condensation complexes known as advanced glycation end-products (AGE). These AGE complex products form on free amino groups, on proteins, on lipids and on DNA (Bucala and Cerami, Adv Pharmacol 23:1-34, 1992; Bucala et al., Proc Natl Acad Sci 90:6434-6438, 1993; Bucala et al., Proc Natl. Acad Sci 81:105-109, 1984). This phenomenon is called "browning" or a "Maillard" reaction and was discovered early in this century by the food industry (Maillard, Ann Chim 5:258-317, 1916). The significance of a similar process in biology became evident only after the discovery of the glycosylated hemoglobins and their increased presence in diabetic patients (Rahbar, Clin Chim Acta 20:381-5, 1968; Rahbar et al., Biochem Biophys Res Commun 36:838-43, 1969). A diabetic patient's AGE level increases markedly as a result of sustained high blood sugar levels and often leads to tissue damage through a variety of mechanisms including alteration of tissue protein structure and function, stimulation of cellular responses through AGE specific receptors and/or the generation of reactive oxygen species (ROS) (for a recent review see Boel et al., J Diabetes Complications 9:104-29, 1995). These AGE have been shown to cause complications in patients suffering from various pathological conditions, including, but not limited to, diabetes mellitus, rheumatoid arthritis, Alzheimer's Disease, uremia and in atherosclerosis in persons undergoing hemodialysis.

Advanced glycation end-products bind to cell surface receptors on a variety of cells including, but not limited to, endothelial cells of the microvasculature, monocytes and macrophages, smooth muscle cells, mesengial cells and neurons through a specific receptor for AGEs, termed RAGE. RAGE is a member of the immunoglobulin super family of cell surface molecules. Increased levels of RAGE are expressed in a number of tissues including, but not limited to, aging tissues, diabetic tissues, the vasculature and the kidney. Activation of RAGE has been implicated in a variety of conditions including, but not limited to, acute and chronic inflammation, in certain complications of diabetes, nephropathy, atherosclerosis and retinopathy, Alzheimer's disease, erectile dysfunction and in tumor invasion and metastases.

The complications associated with each of these aforementioned pathological conditions places a significant burden on afflicted patients. Moreover, these complications have detrimental effects on society in general. As one example, the global prevalence of diabetes mellitus afflicts millions of individuals resulting in significant increases of morbidity and mortality rates. These increased morbidity and mortality rates, together with the great financial burden of treating diabetic complications, are major incentives to search for and develop medications having the potential of preventing or treating complications of the disease.

The compounds of the present invention inhibit the nonenzymatic formation of glycation and dehydration condensation complexes known as advanced glycation end-products (AGE). In one embodiment of the present invention, a method is provided for administering a medication that inhibits the nonenzymatic formation of glycation and dehydration condensation complexes known as advanced glycation end-products (AGE) to a subject in need thereof, comprising providing at least one medication that inhibits the nonenzymatic formation of AGE complexes; and administering the medication to an patient wherein the nonenzymatic formation of AGE complexes is inhibited.

In another embodiment of the method, the administering step comprises a route of administration selected from the group consisting of oral, sublingual, intravenous, intracardiac, intraspinal, intraosseous, intraarticular, intrasynovial, intracutaneous, subcutaneous, intramuscular, epicutaneous, transdermal, conjunctival, intraocular, intranasal, aural, intrarespiratory, rectal, vaginal and urethral. In another embodiment, the administering step comprises providing the medication on an implantable medical device.

While these medications are typically parameter specific medications, they are efficacious in wound healing, in scar reduction and in the treatment of burns. For example, a compound that inhibits the formation of AGE complexes may be directly applied to in a conventional hydrophilic or oleophilic ointment base, or incorporated within, a medical device (i.e., a wound dressing, patch, etc.) and applied to a patient's skin to aid the would healing process.

Any method of administering the medication(s) discussed herein is contemplated. While it is understood by one skilled in the art that the method of administration may depend on patient specific factors, the methods of administration include, but are not limited to, generally parenteral and nonparenteral administration. More specifically, the routes of administration include, but are not limited to oral, sublingual, intravenous, intracardiac, intraspinal, intraosseous, intraarticular, intrasynovial, intracutaneous, subcutaneous, intramuscular, epicutaneous, transdermal, conjunctival, intraocular, intranasal, aural, intrarespiratory, rectal, vaginal, urethral, etc. Typically, an oral route of administration is preferred.

Of course, it is understood that the medication will be administered in the appropriate pharmaceutical dosage, depending on the route of administration. For example, an oral dosage form may be administered in at least one of the following pharmaceutical dosage forms: tablet; capsule; solution; syrup; elixir; suspension; magma; gel; and/or powder. A sublingual preparation may be administered in at least one of the following pharmaceutical dosage forms: tablet; troche; and/or lozenge. A parenteral dosage form may be administered in at least one of the following pharmaceutical dosage forms: solution and/or suspension. An epicutaneous/transdermal dosage form may be administered in at least one of the following pharmaceutical dosage forms: ointment; cream; infusion pump; paste; plaster; powder; aerosol; lotion; transdermal patch/disc/solution. A conjunctival dosage form may be administered in at least one of the following pharmaceutical dosage forms: contact lens insert and/or ointment. An intraocular/intraaural dosage form may be administered in at least one of the following pharmaceutical dosage forms: solution and/or suspension. An intranasal dosage form may be administered in at least one of the following pharmaceutical dosage forms: solution; spray; inhalant and/or ointment. An intrarespiratory dosage form may be administered in at least one of the following pharmaceutical dosage forms: aerosol and/or powder. A rectal dosage form may be administered in at least one of the following pharmaceutical dosage forms: solution; ointment and/or suppository. A vaginal dosage form may be administered in at least one of the following pharmaceutical dosage forms: solution; ointment; emulsion foam; tablet; insert/suppository/sponge. A urethral dosage form may be administered in at least one of the following pharmaceutical dosage forms: solution and/or suppository.

The above-noted dosage form(s) may include at least one medication disclosed herein, either alone or in combination with at least one other medication disclosed herein or with a medication not disclosed herein and/or in combination with at least one inert pharmaceutical excipient. These medications may have any release profile including, but not limited to, an immediate release, a controlled release and/or a delayed release profile.

The medical devices include, but are not limited to, implantable medical devices such as, but not limited to, stents (both vascular and urethral), deposition implants (implantable medication releasing device), and/or a medication delivery pumps. Also, contemplated herein are topically applied medical devices including, but not limited to, patches, gauze, wraps, appliques, dressings, coverings, etc. In the case of a medical device, at least one medication may be releasably applied either to at least a portion of the surface of the device, or to a material applied to the surface of a device. Alternatively, at least one medication may be absorbed and/or adsorbed into or onto the device material so long as the medication may be released from the material at a later time.

The medication may be releasably applied to the medical device via any industrially acceptable method, including, but not limited to, spray coating, a waterfall method, heat annealing, etc., however, spray coating is typically preferred. Alternatively, the medical device may include at least one medication, wherein the medication is absorbed and/or adsorbed into or onto the medical device. This may be done by any industrially acceptable method. Also, it is contemplated herein that a medical device may include both at least one medication releasably applied to the medical device itself and/or a coating applied to the device and at least one medication absorbed and/or adsorbed into or onto the medical device itself.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

In the course of screening different classes of organic compounds for investigation of their possible inhibitory effects on advanced glycation endproducts (AGEs), it has been found that most of the phenylureido substituted phenoxy propionic acid derivatives tested have inhibitory effects and several of these compounds were potent inhibitors of AGE-formation at concentrations much lower than an equally inhibiting concentration of aminoguanidine.

The mechanism by which this class of compounds inhibits glycation, AGE-formation, and crosslinking is yet to be known in full. Two major mechanisms, transient-metal-chelation such as copper and iron, and scavenging or trapping of reactive carbonyl intermediates have been proposed to be responsible for AGE-inhibitory function of known AGE-inhibitors.

The mechanism of the inhibitory activities of guanidino compound inhibitors such as two known inhibitors of glycation (aminoguanidine and metformin) is that they are postulated to trap MG and other alpha.-dicarbonyl intermediates of glycation. A most recent study has documented the reaction of metformin with MG and glyoxal (GO), forming guanidino-dicarbonyl adducts further supporting this idea (Ruggiero-Lopez et al., 1999).

Using known assay methods specific for the early (Amadori) and late (post-Amadori) stages of glycation revealed some inhibitors to have greater effects in the early stage and some in the late stage of glycation. However, most of the inhibitor compounds we have investigated are multistage inhibitors. The reaction of reducing sugars with .alpha.- and .epsilon.-amino groups of proteins is not a random process but rather a site specific reaction which depends on the nature and the vicinity of these chemical groups. The future task is to specifically define the site and/or sites of interaction of an inhibitor compound in the complex series of reactions and intermediate substrates, leading to AGE formation and cross-linking.

The development of the novel inhibitors of glycation, AGE formation, and AGE-protein crosslinking expands the existing arsenals of inhibitors of glycation reaction that can find therapeutic applications for the prevention of diabetic complications, as well as the prevention of other diseases associated with increased glycation of proteins or lipids. Furthermore, the availability of these compounds may prove useful as tools to study the cascade of reactions and intermediate substrate in the process of AGE-formation and AGE-protein cross-linking.

The compounds of the invention and their useful compositions utilized in the present invention contain agents capable of reacting with the highly active carbonyl intermediate of an early glycation product thereby preventing those early products from later forming the advanced glycation endproducts or in the alternative as agents for "breaking" or reversing the AGE complexes after they form protein crosslinked compounds which cause protein aging. Doses of 1-1000 mg per day may be used to prevent the formation of AGE complexes or to break AGE complexes depending on the desired effect and the observed response in a patient. The formation of AGE has been linked to several pathologies which may be treated according to the invention including chronic inflammation, neuropathy, atherosclerosis, retinopathy, Alzheimer's disease, erectile dysfunction and diabetes. The compounds of the invention are useful for the treatment of pre-diabetes, Type I and Type II diabetes as well as the prevention and/or treatment of diabetic complications such as elevated cholesterol, retinopathy, kidney damage, circulatory disorders, neuropathy and the like. The compounds of the invention also have activity against rheumatoid arthritis, Alzheimer's disease, Wilson's disease, atherosclerosis, neurodegenerative diseases, such as multiple sclerosis, neurotoxins and metabolic syndrome. An oral dose for these conditions is preferred but other routes of administration may be utilized. An effective amount of an oral dose will be from 1-1000 mg daily preferable given in divided doses. It is presently contemplated that a dose of 250-500 mg daily would be preferred.

Other utilities envisioned for the present invention are prevention of aging of the skin by exerting an anti-aging effect that reduces wrinkles and makes the skin smoother. The compounds also inhibit spoilage of proteins in foodstuffs such as the browning reaction seen in certain fruits. The present agents are also useful in the area of oral hygiene as they prevent discoloration of teeth and may be used as solutions or dispersions in water or a cream at a concentration of 0.1 to 10% by weight. and used as a cosmetic on the skin to improve the smoothness, texture, appearance and to prevent or treat aging of the skin. A particular use is the application of compounds to skin for the purpose of increasing the collagen content which will inhibit or reverse environmental aging effects. The compounds of the invention reduce the amount of MMP9 in the skin. They may be used systemically or topically for scleroderma, acne, psoriasis, inflammation, antioxidant effects or for chelation of metals. For topical use, the compounds may be added to hydrophilic or oleophilic cosmetic bases in amounts of 0.01 to 10% by weight, and preferably 1-5% or they may be applied as a solution, dispersion or gel. For systemic use, the compounds may be administered orally at a dose of 1-1000 mg daily in divided doses. The dose will be adjusted depending on the observed effect using conventional dosing techniques.

The compounds of the invention have PPAR activity which is an acronym for peroxisome proliferator activated receptor which are a group of receptor isoforms which exist across biology. They are intimately connected to cellular metabolism (carbohydrate, lipid and protein) and cell differentiation. They are also transcript factors. Several types of PPARs have been identified: alpha, gamma 1, 2 and 3 as well as delta or beta. The alpha form is expressed in liver, kidney, heart, adipose tissues as well as in other tissues. The gamma 1 form is expressed in virtually all tissues including heart, muscle, colon, kidney, pancreas and spleen tissues. The gamma 2 form is expressed mainly in adipose tissue (30 amino acids or longer while gamma 3 is expressed in macrophage, large intestine and white adipose tissue. Delta is expressed in many tissues but mainly in brain, adipose tissue and skin. PPARs dimerize with the retinoid receptor and bind to specific regions on the DNA of the largest genes and when PPAR binds to its ligand, transcription of target genes is increased or decreased depending on the gene. The PPAR activity of the compounds of the invention is a property that confirms that the compounds of the invention are useful as antidiabetic compounds in the manner that the PPAR active compound pioglitazone is useful when administered orally to diabetics. The dose may be from 1 to 1000 mg orally and preferably 250-500 mg orally, daily basis given in divided doses.

To aid in the administration, the compound may be combined with a pharmaceutical acceptable diluent or carrier to form a pharmaceutical dosage form. The dosage form can be a liquid, solid, gel for immediate release or controlled release. Common pharmaceutical diluents or carriers are described in the Handbook of Pharmaceutical Excipients, 4$^{th}$ addition, the United States Pharmacopiea, and Remington's Pharmaceutical Science.

Compounds of the present invention can be prepared as follows:

Example 1

4-benzylamino-phenoxyisobutyric acid

A mixture of 1.95 g (0.01 mole) of 4-aminophenoxyisobutyric acid, 25 ml of ethanol, 1.76 g (0.02 mole) of potassium carbonate and 1.2 ml (0.01 mole) of benzyl bromide was stirred and refluxed for 24 hours. Most of the ethanol was evaporated. The residue was dissolved in water, charcoaled, filtered, and acidified water acetic acid to give an oily material which by cooling turned into a solid with a melting point of 194-196° C. The structure (shown below as Formula EX1) was confirmed by NMR spectroscopy.

EX 1

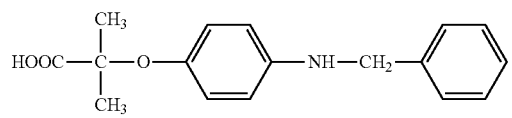

Example 2

4-(4-chloro)benzylamino-phenoxyisobutyric acid

A mixture of 1.28 ml (10 mole) of 4-chlorobenzylchloride, 1.95 g (10 mole) 4-aminophenoxyisobutyric acid, 2.76 g (20 mole) potassium carbonate and 20 ml ethanol was refluxed and stirred for 24 hours. The mixture was treated as in Example 1 giving a solid with a melting point of 164-166° C. The structure (shown below as Formula EX2) was confirmed by NMR spectroscopy.

Ex 2

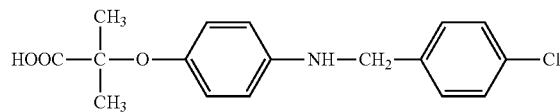

Congeners similar to Formula EX2 wherein the chlorine is in the 2 or 4 position can also be prepared by the above procedure by appropriate selection of the starting benzylhalide. Compounds similar to the above described chloride congenes wherein the chlorine is replaced by another halogen such as fluorine or bromine, or a hydrocarbon such as a phenyl, phenoxy or a straight, branched or cyclic alkyl or alkyoxy of 1-6 carbon can also be prepared according to the aforementioned procedure by appropriate selection of the starting substituted benzylhalide. Such a procedure and selection is well within the ability of those skilled in the art. Some of the compounds that have been prepared include, 4-(2-chloro)benzylaminophenoxy isobutyric acid; 4-(3-chloro) benzylaminophenoxy isobutyric acid; 4-(2-fluoro)benzylaminophenoxy isobutyric acid; 4-(3-fluoro) benzylaminophenoxy isobutyric acid; 4-(4-fluoro) benzylaminophenoxy isobutyric acid; 4-(3-methyl) benzylaminophenoxy isobutyric acid; 4-(4-methyl) benzylaminophenoxy isobutyric acid; 4-(3,4-dimethyl) benzylaminophenoxy isobutyric acid; 4-(4-methoxy) benzylaminophenoxy isobutyric acid; and 4-(4-phenoxy) benzylaminophenoxy isobutyric acid.

Example 3

4-(3,4 dichloro)benzylamino-phenoxyisobutyric acid

A mixture of 1.4 ml (10 mole) of 3,4-dichlorobenzylchloride, 1.95 g (10 mole) 4-aminophenoxyisobutyric acid, 2.75 g (20 mole) potassium carbonate and 25 ml ethanol was refluxed and stirred for 24 hours. The mixture was treated as in Example 1 giving a solid with a melting point of 144-146° C. The structure (shown below as Formula EX3) was confirmed by NMR spectroscopy. The yield was approximately 84%

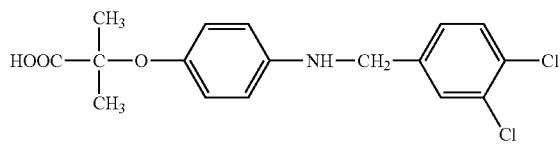

Ex 3

Congeners similar to Formula EX3 wherein the chlorine are in the 2,3; 2,5; 2,6 and 3,5 position can also be prepared by the above procedure by appropriate selection of the starting benzylhalide. Compounds similar to the above described chlorides wherein the chlorine is replaced by another halogen such as fluorine or bromine, or a hydrocarbon such as a phenyl, phenoxy or a straight, branched or cyclic alkyl or alkyoxy of 1-6 carbon can also be prepared according to the aforementioned procedure by appropriate selection of the starting substituted benzylhalide. Such a procedure and selection is well within the ability of those skilled in the art.

Example 4

4-(2-chloro, 6-fluoro)benzylamino-phenoxyisobutyric acid

A mixture of 1.28 ml (10 mole) of 2-chloro, 6-fluorobenzylchloride, 1.95 g (10 mole) 4-aminophenoxyisobutyric acid, 2.76 g (20 mole) potassium carbonate and 25 ml ethanol was refluxed and stirred for 24 hours. The mixture was treated as in example 1 giving a solid with a melting point of 173-175° C. The structure (shown below as Formula EX4) was confirmed by NMR spectroscopy. The yield was approximately 80%

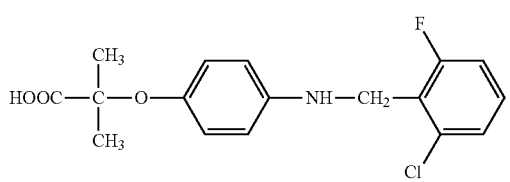

EX 4

Congenes similar to Formula EX4 wherein the chlorine and fluorine are in the 2,3; 2,5; 2,6 and 3,5 position can also be prepared by the above procedure by appropriate selection of the starting benzylhalide. Compounds similar to the above described di-hetero substituted benzyl compounds wherein either the chlorine and/or fluorine is replaced by another halogen such as bromine, or a hydrocarbon such as a phenyl, phenoxy or a straight, branched or cyclic alkyl or alkyoxy of 1-6 carbon can also be prepared according to the aforementioned procedure by appropriate selection of the starting substituted benzylhalide. Such a procedure and selection is well within the ability of those skilled in the art.

Example 5

4-(1-phenethyl amino)-phenoxyisobutyric acid

A mixture of 1.4 ml (0.01) of 1-phenethylbromide, 1.95 g (0.01 mole) 4-aminophenoxyisobutyric acid, 2.75 g (20 mole) potassium carbonate and 25 ml ethanol was refluxed and stirred for 24 hours. The mixture was treated as in Example 1 giving a white crystalline powder with a melting point of 133-135° C. The structure (shown below as Formula EX5) was confirmed by NMR spectroscopy. The yield was approximately 73%

EX 5

HOOC—C(CH$_3$)(CH$_3$)—O—C$_6$H$_4$—NH—CH$_2$—CH$_2$—C$_6$H$_5$

Example 6

4-(1-napthylmethlaminophenoxyisobutyric acid)

A mixture of 1.76 g (0.01) of 1-chloromethylnapthalene, 1.95 g (0.01 mole) of 4-aminophenoxyisobutyric acid, 2.76 g (0.01 mole) potassium carbonate and 30 ml ethanol was refluxed and stirred for 24 hours. The structure of the resulting compound is shown below as Formula EX6

EX 6

HOOC—C(CH$_3$)(CH$_3$)—O—C$_6$H$_4$—NH—CH$_2$—(naphthyl)

Example 7

4-tetramethylene aminophenoxyisobutyric acid

A mixture of 1.2 ml of 1,4-dibromobutane, 1.95 g 4-aminophenoxyisobutyric acid, 5.3 g potassium carbonate and 50 ml ethanol was refluxed and stirred for 38 hours. After evaporation of most of the ethanol, some unreacted dibromobutane and some water were added to dissolve the solid. The solution was acidified with acetic acid and charcoaled. A solid with a melting point of 94-96° C. was formed. The solid was soluble in ethylacetate and chloroform and the structure was confirmed by NMR spectroscopy. The yield was approximately 60%.

Example 8

Compounds of the following Formula, EX8 are prepared by reacting any aromatic aminophenoxy isobutyric acid compounds described above in Examples 1-7 with a substituted isocyanates in molar ratios to give the corresponding disubstituted ureas

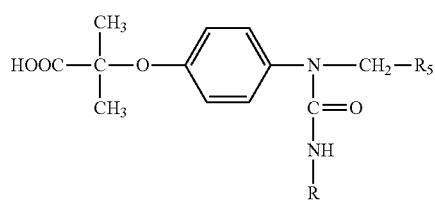

EX 8

Wherein R is an aromatic or aliphatic preferably a phenyl or a straight, branched or cyclic alkyl with 1 to 6 carbon atoms and $R_5$ is the same as defined above, preferably a napthyl or substituted phenyl as described in Examples 1-7.

Example 9 benzene-1,4-bis methyleneaminophenoxyisobutyric acid

A mixture of 0.54 g (0.025 moles) of dichloro-p-xylene, 1.4 (10 moles) of 4-aminophenoxyisobutyric acid, 2.7 g potassium carbonate and 25 ml ethanol was refluxed and stirred for 24 hours. The solvent was then evaporated. The residue was washed with 30 ml of water and filtered over cilate and acidified with acetic acid to give a solid. The solid structure was confirmed by NMR spectroscopy and is shown below as Formula EX9. The solid had a melting point of 164-166° C. The yield was approximately 96%.

Example 11

4-[(N2-benzyl)-4-phenylureidophenoxyisobutyric] acid

While stirring an ice cold solution of 2 mmoles of 4-aminophenoxyisobutyric acid, 2.2 ml of 2N NaOH and 10 ml water about 2.2 mmoles (approximately 0.25 ml) of phenyl isocyanate was added dropwise. After approximately 1 hour a few additionally drops of 2N NaOH was added to the solution to adjust the pH to about 10-12. The solution was charcoaled and filtered and acidified with AcOH or dilute HCl to precipitate the named compound. The solid had a melting point of 82-84° C. The yield was approximately 74%.

Example 12

N,N'-hexylureido-bis-3,4-dichlorophenoxyisobutyric acid

To a molar equivalent of 3,4-dichlorobenzylaminophenoxyisobutyric acid in a mixture of ethyl acetate and triethylamine (10/1), a 1/2 molar ratio of 1,6-di hexyl isocyanate was slowly added. After ½ hour the mixture was warmed to 75° C. After ½ hour of warming, the solvent was evaporated under reduced pressure. The residue was acidified with dilute HCl to give a precipitate. The solid structure was confirmed by NMR spectroscopy and is shown below as Formula EX12. The solid had a melting point of 159-160° C. The yield was approximately 87-90%.

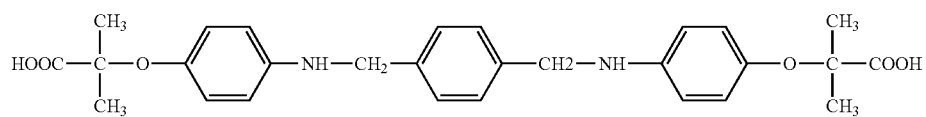

EX 9

Example 10 benzene-1,3-bis methyleneaminophenoxyisobutyric acid

Benzene-1,3-bis methyleneaminophenoxyisobutyric acid was prepared according to the procedure described in Example 9 except alpha-alpha-dichloro m-xylene was used in place of the dichloro-p-xylene. The solid structure was confirmed by NMR spectroscopy and is shown below as Formula EX10. The solid had a melting point of 160-162° C. The yield was approximately 88%.

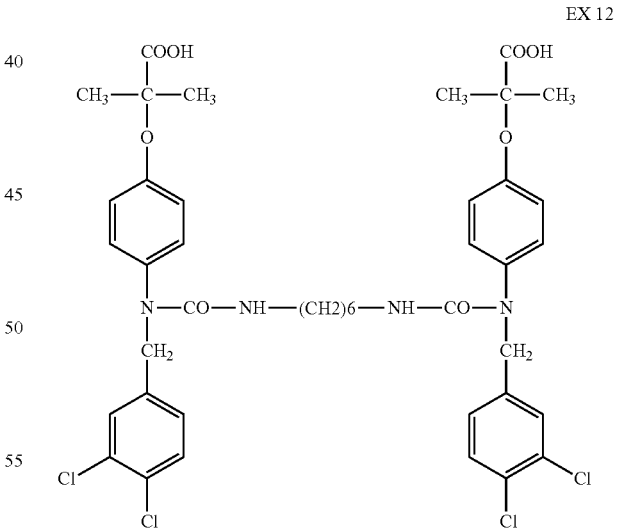

EX 12

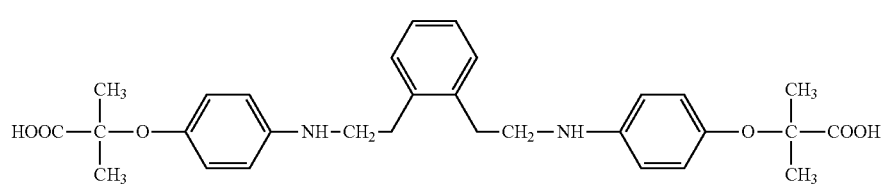

EX 10

Figure 2:
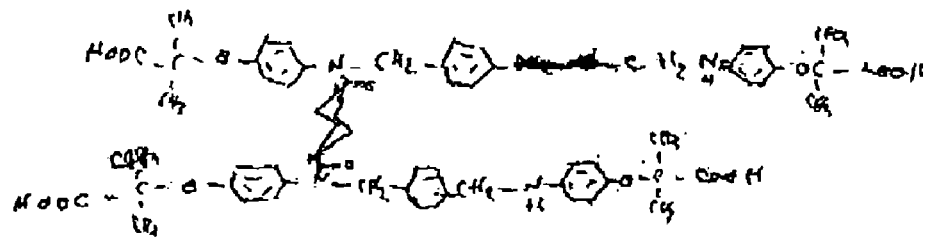
FIG. 2 shows the structure of one embodiment of the present invention.
Figure 3:
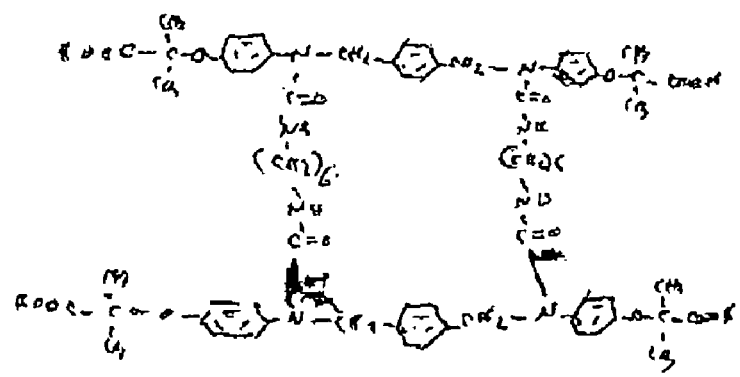
FIG. 3 shows the structure of one embodiment of the present.
Figure 4:
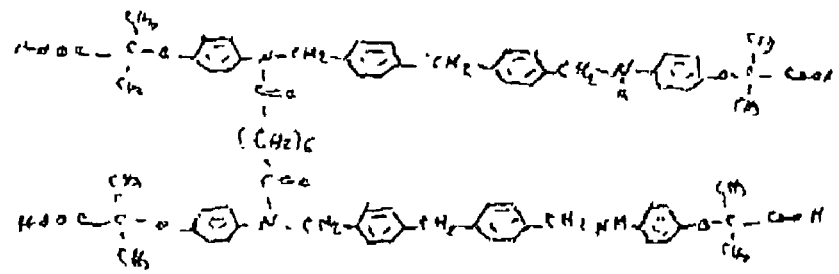
FIG. 4 shows the structure of one embodiment of the present invention.
Figure 5:
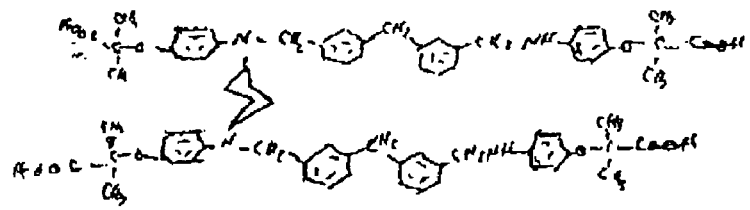
FIG. 5 shows the structure of one embodiment of the present invention.
Figure 6:
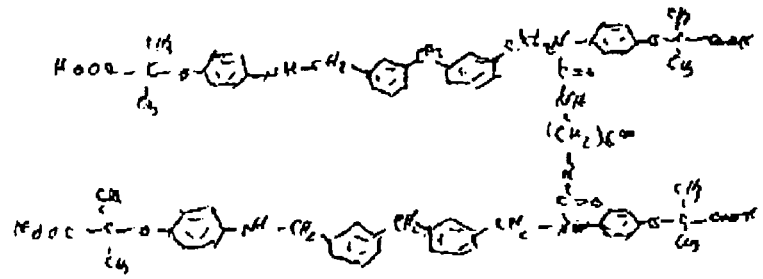
FIG. 6 shows the structure of one embodiment of the present invention.
Figure 7:
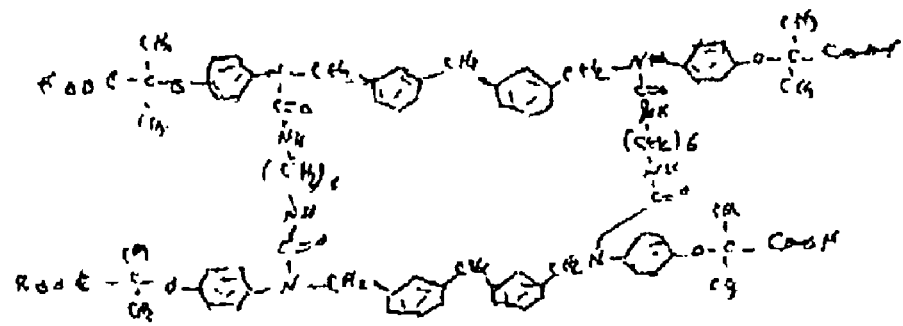
FIG. 7 shows the structure of one embodiment of the present invention.
Figure 8:
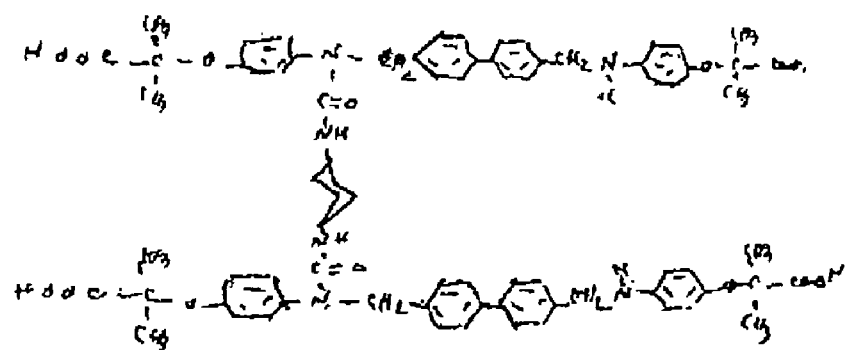
FIG. 8 shows the structure of one embodiment of the present invention.
Figure 9:
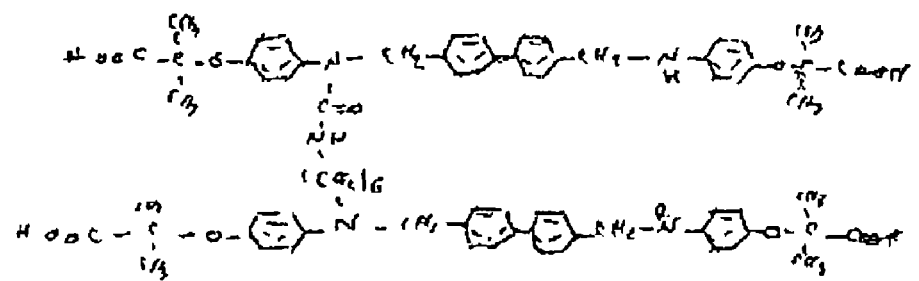
FIG. 9 shows the structure of one embodiment of the present invention.
Figure 10:
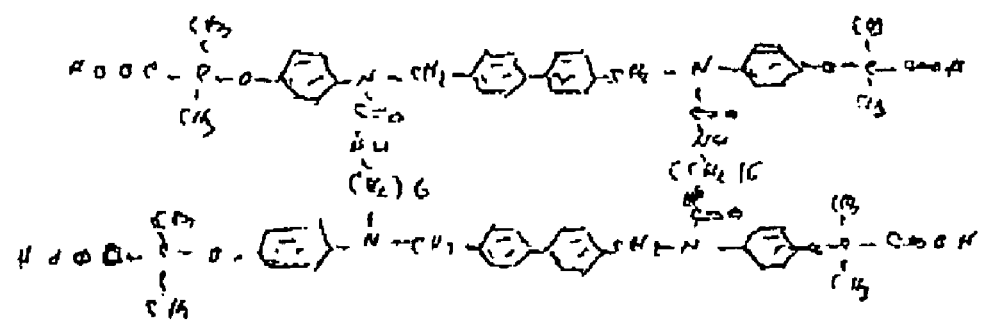
FIG. 10 shows the structure of one embodiment of the present invention.

The compounds shown in FIGS. 1-10 were prepared according to the procedures outlined above in Examples 1-12 using the appropriate substituted isocyanates and substituted aromatics.

While the invention has been disclosed in this patent application by reference to the details of preferred embodiments of the invention, it is to be understood that the disclosure is intended in an illustrative rather than in a limiting sense, as it is contemplated that modifications will readily occur to those skilled in the art, within the spirit of the invention and the scope of the appended claims.

We claim:

1. A compound of the formula:

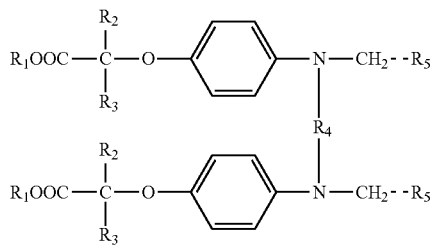

wherein $R_1$ is selected from hydrogen and a pharmaceutically acceptable cation;
$R_2$ and $R_3$ are independently selected from hydrogen and lower alkyl of 1 to 5 carbon atoms;
$R_4$ is —CO—NH$(R_6)_n$NH—CO—, —CO—NH$(R_6)_n$—CO—, —CO—NH$(R_6)_n$—, —CO—$(R_6)_n$—CO—, or —$(R_6)_n$,
wherein $R_6$ is phenylene, or a straight, branched or cyclic alkyl with 1 to 6 carbon atoms and n is a whole integer from 1 to 4;
$R_5$ is independently selected from phenylene; mono-, di-, and tri-alkyl or haloalkyl phenylene of 1 to 5 carbon atoms; mono-, di- and tri halophenylene; phenylene-CH$_2$-phenylene or a phenoxyisobutyric acid derivative of the formula;

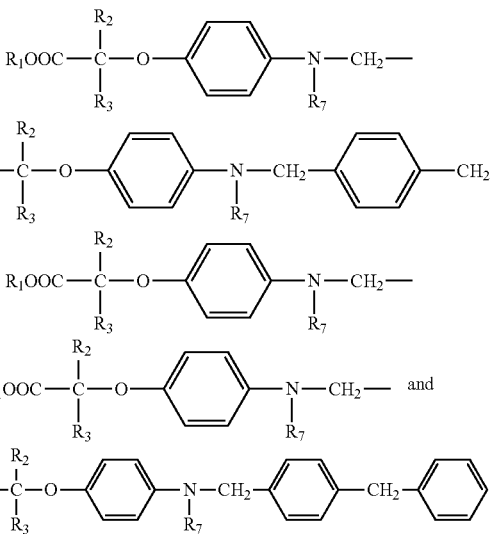

wherein $R_1$, $R_2$ and $R_3$ are as previously defined and $R_7$ is hydrogen, lower alkyl of 1-4 carbon atoms or $R_4$ when both $R_5$ moieties are the phenoxyisobutyric acid derivatives.

2. The compound as defined in claim 1 wherein $R_6$ is phenylene.

3. The compound as defined in claim 1 wherein $R_6$ is an alkyl with 1 to 6 carbon atoms.

4. The compound as defined in claims 3 wherein the alkyl is cyclic.

5. The compound as defined in claim 1 wherein $R_2$ and $R_3$ are lower alkyls of 1 to 5 carbons.

6. The compound as defined in claim 5 wherein $R_2$ and $R_3$ are methyl.

7. The compound as defined in claim 1 wherein $R_5$ is a mono-, di-, or trihalophenylene.

8. A pharmaceutical composition which comprises a compound as defined in claim 1 and a pharmaceutically acceptable diluent.

* * * * *